United States Patent
Dellamorte et al.

(10) Patent No.: US 9,556,100 B2
(45) Date of Patent: Jan. 31, 2017

(54) METHOD AND CATALYST COMPOSITE FOR PRODUCTION OF VINYL ACETATE MONOMER

(71) Applicant: BASF Corporation, Florham Park, NJ (US)

(72) Inventors: Joseph C. Dellamorte, Beachwood, OH (US); Ronald T. Mentz, Erie, PA (US)

(73) Assignee: BASF CORPORATION, Florham Park, NJ (US)

( * ) Notice: Subject to any disclaimer, the term of this patent is extended or adjusted under 35 U.S.C. 154(b) by 443 days.

(21) Appl. No.: 13/932,233

(22) Filed: Jul. 1, 2013

(65) Prior Publication Data

US 2014/0039218 A1  Feb. 6, 2014

Related U.S. Application Data

(60) Provisional application No. 61/667,188, filed on Jul. 2, 2012.

(51) Int. Cl.
| | |
|---|---|
| *B01J 21/00* | (2006.01) |
| *C07C 51/25* | (2006.01) |
| *B01J 37/02* | (2006.01) |
| *B01J 37/06* | (2006.01) |
| *B01J 37/18* | (2006.01) |
| *B01J 23/56* | (2006.01) |
| *B01J 23/58* | (2006.01) |

(Continued)

(52) U.S. Cl.
CPC ............... *C07C 51/25* (2013.01); *B01J 23/56* (2013.01); *B01J 23/58* (2013.01); *B01J 35/008* (2013.01); *B01J 35/1019* (2013.01); *B01J 37/0203* (2013.01); *B01J 37/0234* (2013.01); *B01J 37/06* (2013.01); *B01J 37/18* (2013.01); *C07C 67/055* (2013.01)

(58) Field of Classification Search
CPC ......... C07C 51/25; C07C 67/055; B01J 23/56; B01J 23/58; B01J 35/008; B01J 35/1019; B01J 37/0203; B01J 37/0234; B01J 37/06; B01J 37/18
USPC ...................................................... 502/262
See application file for complete search history.

(56) References Cited

U.S. PATENT DOCUMENTS

| | | | |
|---|---|---|---|
| 4,048,096 | A | 9/1977 | Bissot |
| 5,002,918 | A | 3/1991 | Deller et al. |

(Continued)

FOREIGN PATENT DOCUMENTS

| | | |
|---|---|---|
| CN | 101262944 | 9/2008 |
| CN | 101730584 | 6/2010 |
| WO | WO2006-136781 | 12/2006 |

OTHER PUBLICATIONS

International Preliminary Report on Patentability dated Jan. 6, 2015.
(Continued)

*Primary Examiner* — Colleen Dunn
*Assistant Examiner* — Haytham Soliman
(74) *Attorney, Agent, or Firm* — Foley & Lardner LLP

(57) ABSTRACT

Provided are catalyst composites useful for the production of vinyl acetate monomer, as well as methods of making using same. The catalyst composites may comprise a support comprising silica and about 1 to about 3 wt-% alumina, wherein the support has a surface area of about 175 to about 300 m²/g; and an eggshell layer on the support comprising Pd and Au.

7 Claims, 1 Drawing Sheet

(51) Int. Cl.
*B01J 35/00* (2006.01)
*B01J 35/10* (2006.01)
*C07C 67/055* (2006.01)

(56) References Cited

U.S. PATENT DOCUMENTS

| | | |
|---|---|---|
| 5,225,388 A | 7/1993 | Wunder et al. |
| 5,808,136 A | 9/1998 | Tacke et al. |
| 5,968,860 A | 10/1999 | Herzog |
| 6,156,927 A | 12/2000 | Halcom et al. |
| 2001/0048970 A1 | 12/2001 | Hagemeyer et al. |
| 2003/0148883 A1 | 8/2003 | Khanmmamedova et al. |
| 2003/0195114 A1 | 10/2003 | Tacke et al. |
| 2008/0249331 A1* | 10/2008 | Allan ................ B01J 21/12 560/245 |
| 2010/0197956 A1* | 8/2010 | Hagemeyer ....... B01J 21/16 560/208 |
| 2011/0071312 A1* | 3/2011 | Johnston ........... C07C 29/149 560/261 |

OTHER PUBLICATIONS

Examination Report and Written Opinion received for Singapore Application No. 11201500029V issued Apr. 19, 2016, 11 pages.
Extended Search Report received for European Patent Application No. 13813659.3 issued Feb. 11, 2016, 8 pages.
First Office Action received for Chinese Patent Application No. 201380045181.3 issued Dec. 4, 2015, 17 pages with English translation.

* cited by examiner

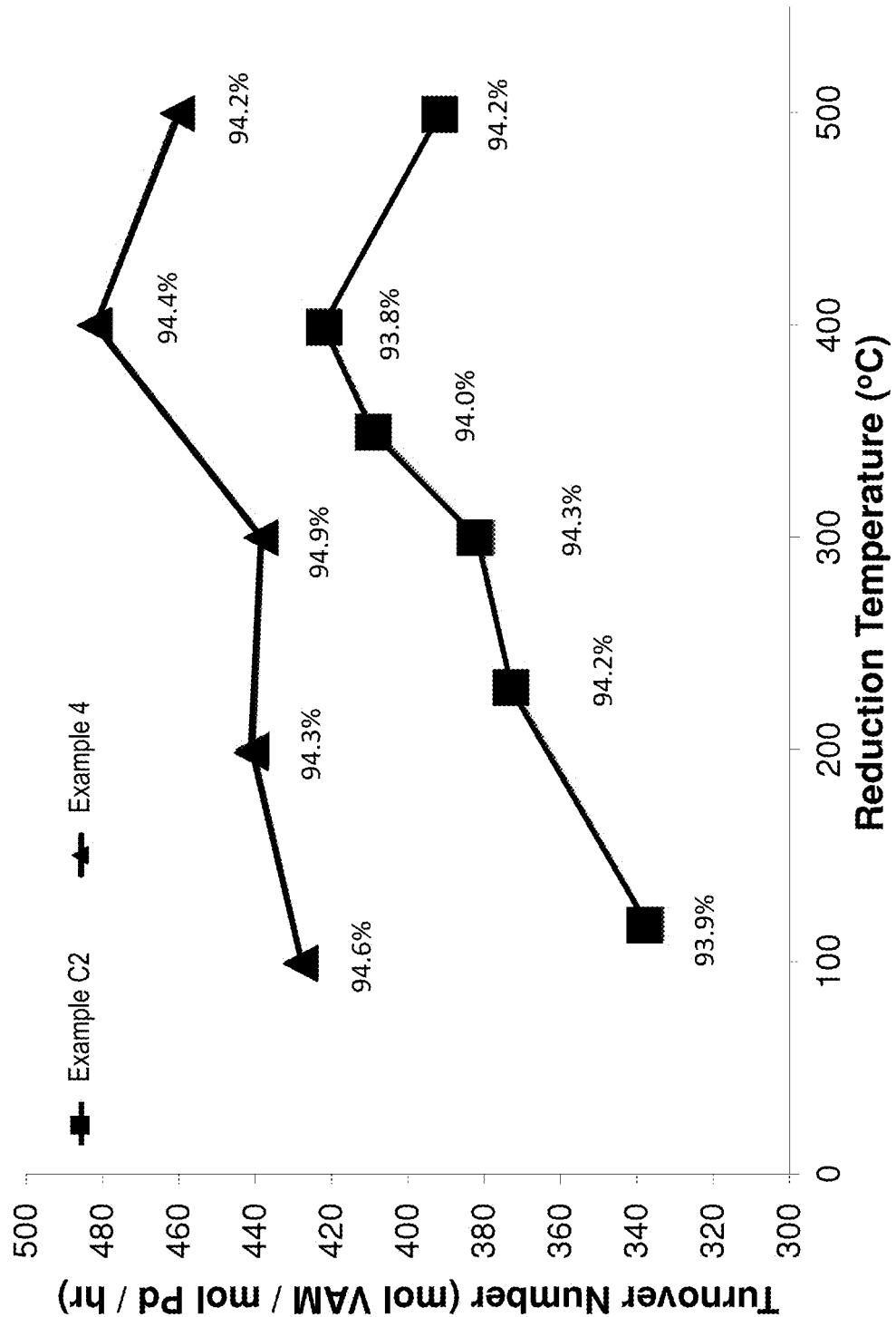

METHOD AND CATALYST COMPOSITE FOR PRODUCTION OF VINYL ACETATE MONOMER

CROSS-REFERENCE TO RELATED APPLICATIONS

This application claims priority to U.S. Provisional Application No. 61/667,188, filed Jul. 2, 2012, the entire contents of which are herein incorporated by reference.

TECHNICAL FIELD

Aspects of the invention relate to catalyst compositions, methods for preparing catalysts and methods using the catalyst to produce vinyl acetate monomer.

BACKGROUND

Vinyl acetate monomer (VAM) is a compound having the formula $CH_3COOCH=CH_2$. According to some estimates, world production capacity for VAM was 4.7 million metric tons in 2010. VAM is an important ingredient in a wide variety of products, including polymers and as an intermediate in coatings, textiles, paints, etc. For example, VAM is the precursor to polyvinyl acetate, which is an important vinyl polymer. Polyvinyl acetate is used in many applications, including several relating to glues and adhesives.

VAM is typically synthesized by reacting ethylene and acetic acid with oxygen in the gas phase and in the presence of a palladium and/or gold catalyst with potassium acetate promoter. The reaction is typically carried out using a fixed bed reactor filed with catalyst composites. However, there is a continuing need for catalyst composites which are more active than previously used composites.

SUMMARY

One aspect of the invention relates to a catalyst composite. comprising: a support comprising silica and about 1 to about 3 wt-% alumina, wherein the support has a surface area of about 175 to about 300 $m^2/g$; an eggshell layer on the support comprising Pd and Au. In one or more embodiments, the catalyst composition comprises about 2 wt-% alumina. In one or more embodiments, the support has a surface area of about 200 to about 250 $m^2/g$. In a further embodiment, the support has a surface area of about 225 $m^2/g$. Various embodiments are listed below. It will be understood that the embodiments listed below may be combined not only as listed below, but in other suitable combinations in accordance with the scope of the invention.

In one or more embodiments, the eggshell catalyst layer may comprise gold present in an amount of about 0.9 to about 5 g per liter of catalyst composition and palladium in an amount of about 3 to about 10 g per liter of catalyst composition. In some embodiments, the eggshell layer further comprises potassium acetate in an amount of about 25 to about 60 g per liter of catalyst composition.

A second aspect of the invention relates to a method of making a catalyst composite. The method comprises providing a support comprising silica and about 1 to about 3 wt-% alumina, wherein the support has a surface area of about 175 to about 300 $m^2/g$; depositing Pd and Au onto the support to provide a support with an eggshell catalyst layer; impregnating the support with eggshell catalyst layer with potassium acetate; and reducing the support with eggshell catalyst layer at a temperature of about 90° C. to about 150° C. in a forming gas comprising hydrogen gas and nitrogen gas to form a catalyst composite.

In one or more embodiments, the hydrogen gas and nitrogen gas are present in a ratio range from about 5 to about 1 to about 1 to about 5. In some embodiments, the support with eggshell catalyst layer is reduced for about one to about four hours. In one or more embodiments, the support has a surface area of about 200 to about 250 $m^2/g$. In some embodiments, the support has a surface area of about 225 $m^2/g$. In one or more embodiments, the gold present in an amount of about 0.9 to about 5 g per liter of catalyst composition and palladium is present in an amount of about 3 to about 10 g per liter of catalyst composition. In some embodiments, depositing Pd and Au onto the support to provide a support with eggshell catalyst layer comprises impregnating the support with a solution containing chloride salts of Pd and Au and subsequently contacting the support with a basic solution. In one or more embodiments, the method further comprises washing and drying the support with eggshell catalyst layer. In some embodiments, impregnating the support with eggshell catalyst layer with potassium acetate comprises impregnating the support with a solution containing potassium acetate and drying said support.

A third aspect of the invention relates to a method of making a catalyst composite. The method comprises providing a support comprising silica and about 1 to about 3 wt-% alumina, wherein the support has a surface area of about 175 to about 300 $m^2/g$; depositing Pd and Au onto the support to form a support with eggshell catalyst layer; reducing the support with eggshell catalyst layer at a temperature of about 200 to about 500° C. in a reducing gas comprising about 20% to about 100% hydrogen gas for about 1 to about 4 hours; and impregnating the support with eggshell catalyst layer with potassium acetate.

There are many variants of the method. For example, in one or more embodiments, the eggshell catalyst layer is reduced for about 2 to about 3 hours. In some embodiments, the reducing gas further comprises nitrogen gas or ethylene. The nitrogen and hydrogen gases may be present in a ratio from about 5 to 1 to almost pure hydrogen. In a third embodiment, depositing Pd and Au onto the support to form a catalyst layer on the support comprises impregnating the support with a solution containing chloride salts of Pd and Au and subsequently contacting the support with a basic solution.

Additionally, any of the variants in the composite discussed above can be used. For example, in a fourth embodiment, the support has a surface area of about 200 to about 250 $m^2/g$. In a some embodiments, the support has a surface area of about 225 $m^2/g$. In one or more embodiments, the gold present in an amount of about 0.9 to about 5 g per liter of catalyst composition and palladium is present in an amount of about 3 to about 10 g per liter of catalyst composition.

In a one or more embodiments, the method further comprises washing and drying the support with eggshell catalyst layer. In some embodiments, impregnating the support with eggshell catalyst layer with potassium acetate comprises impregnating the support with a solution containing potassium acetate and drying said support under vacuum.

A fourth aspect of the invention relates to a method of producing vinyl acetate monomer. The method comprises contacting a gas comprising ethylene, acetic acid and oxygen with a catalyst composition comprising: a support comprising silica and about 1 to about 3 wt-% alumina, wherein the support has a surface area of about 175 to about 300 m²/g; and an eggshell catalyst layer comprising gold or palladium.

Again, any variants of the composite discussed above can be used. For example, in one or more embodiments, the catalyst composition comprises about 2 wt-% alumina. In some embodiments, the support has a surface area of about 200 to about 250 m²/g. In one or more embodiments, the support has a surface area of about 225 m²/g. In some embodiments, the eggshell catalyst layer comprises gold and palladium. In one or more embodiments, the gold present in an amount of about 0.9 to about 5 g per liter of catalyst composition and palladium is present in an amount of about 3 to about 10 g per liter of catalyst composition

BRIEF DESCRIPTION OF THE DRAWINGS

The FIGURE shows the space-time-yield of a catalyst composition according to one or more embodiments of the invention and a catalyst composition of the prior art.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

One aspect of the invention relates to a catalyst composite. The catalyst composite comprises a support comprising silica and about 1 to about 3 wt-% alumina, wherein the support has a surface area of about 175 to about 300 m²/g, and an eggshell layer on the support comprising palladium (Pd) and gold (Au).

As used herein, the term "surface area" refers to the internal surface area.

As used herein, the term "eggshell layer," "catalyst layer" or "eggshell catalyst layer" refers to a thin layer of catalyst on the outer regions of the support. It is not necessarily a layer that rests exclusively over the support, but rather that the outer regions of the support contain catalyst. In one or more embodiments, the eggshell layer is continuous around the support. In one or more embodiments, the catalyst penetrates the support at a depth of less than about 500, 450, or 400 µm.

In one or more embodiments, the amount of alumina may range from about 1 to about 3 wt-% alumina. In a further embodiment, the amount of alumina may range from about 1.5 to about 2.5 wt-% alumina. In a yet further embodiment, the amount of alumina may be about 2 wt-% alumina.

In some embodiments, surface area of the support may range from about 175 to about 300 m²/g. In a further embodiment, the surface area may range from about 200 to about 250 m²/g. In yet a further embodiment, the surface area of the support may be about 225 m²/g.

In one or more embodiments, the catalyst used comprises gold and/or palladium. In one or more embodiments, Au and Pd are present in a ratio of Au to Pd of about 0.3 to about 0.5. The amount of Au and/or Pd may be described as amount per liter of total catalyst composition. Thus, in one or more embodiments, Pd is present in an amount of about 3 to about 10 grams per liter of catalyst composition. In one or more embodiments, Au is present in an amount of about 0.9 to about 5 grams per liter of catalyst composition.

In one or more embodiments, the catalyst composite comprises about 25 to about 60 g/L of potassium acetate. In further embodiments, the catalyst composite comprises about 35 to about 45 g/L.

Preparation

Another aspect of the invention relates to a process for making one or more of the catalyst composites described herein. The method comprises providing a support comprising silica and about 1 to about 3 wt-% alumina, wherein the support has a surface area of about 175 to about 300 m²/g; depositing Pd and Au onto the support to provide a support with an eggshell catalyst layer; impregnating the support with an eggshell catalyst layer with potassium acetate; and reducing the resulting catalyst precursor on the support at about 90° C. to about 150° C. in a forming gas comprising hydrogen gas and nitrogen gas to form a catalyst composite.

In one or more embodiments, a spherical support is used. The size of the support may be any that is otherwise suitable for use in the production of vinyl acetate monomer. Examples of suitable supports have a particle diameter of from about 3 to about 7 mm, or more specifically a diameter of from about 4.5 to about 6 mm, or even more specifically from about 5.1 to about 5.6 mm.

Any of the above-described variants in the catalyst support may be used. Thus, for example, the support may have a surface area of about 200 to about 250 m²/g, or surface area of about 225 m²/g. In one or more embodiments, the support may comprise about 2 wt-% alumina.

In one or more embodiments, Pd and Au may be deposited with an aqueous solution containing compounds of both elements. Thus, in one embodiment, depositing Pd and Au onto the support to form a catalyst layer on the support comprises impregnating the support with a solution containing chloride salts of Pd and Au and subsequently contacting the support with a basic solution. Alternatively, separate solutions may be used, one containing a Pd compound and the other a Au compound. Examples of suitable water-soluble Pd compounds include, but are not limited to, palladium (II) chloride, sodium palladium (II) chloride and palladium (II) nitrate. Examples of suitable water-soluble Au compounds include, but are not limited to, gold (III) chloride and tetrachloroauric (III) acid.

The resulting amounts of catalyst can be calculated to achieve the desired amount of Au and/or Pd. Thus, for example, in one or more embodiments, the Pd is present in an amount of about 3 to about 10 g per liter of catalyst composition and/or the Au is present in an amount of about 0.9 to about 5 g per liter of catalyst composition. In one or more embodiments, the ratio of gold to palladium is about 0.3 to about 0.5.

The process may further comprise washing the support with eggshell layer to remove residual alkali metals and halogens leftover from the precursors and then drying the support with eggshell catalyst layer.

In one or more embodiments, the support with an eggshell catalyst layer is impregnated with potassium acetate. It should be noted that impregnation with potassium acetate may be carried out either before or after reduction of the support with eggshell layer in forming gas. This may be carried out after depositing Pd and/or Au by covering the eggshell catalyst layer with a solution of the potassium acetate. In one embodiment, impregnating the catalyst layer on the support with potassium acetate comprises impregnating the support with a solution containing potassium acetate and drying said support. In one embodiment, drying the support comprises drying under vacuum.

The support with eggshell catalyst layer may then be reduced at about 90° C. to about 150° C. in a gas mixture comprising hydrogen gas and nitrogen gas. In a further embodiment, the temperature range is from about 100 to about 140, 130 or 120° C. In a further embodiment, the temperature is about 118° C. In one or more embodiment, the gas mixture contains from about 4% hydrogen to about 100% hydrogen. In some embodiments, the catalyst layer on the support is reduced for about one to about four hours. In one or more embodiments, the gas mixture contains more than 20% hydrogen.

In another aspect, the invention relates to a second method of making the catalyst composites described herein. The method comprises providing a support comprising silica and about 1 to about 3 wt-% alumina, wherein the support has a surface area of about 175 to about 300 $m^2/g$; depositing Pd and Au onto the support to form an support with eggshell catalyst layer; reducing the support with eggshell catalyst layer at a temperature of about 200 to about 500° C. in a reducing gas comprising about 4% to about 100% hydrogen gas for about 1 to about 4 hours; and impregnating the support with eggshell catalyst layer with potassium acetate.

In one or more embodiments, a spherical support is used. The size of the support may be any that is otherwise suitable for use in the production of vinyl acetate monomer. Examples of suitable supports have a particle diameter of from about 3 to about 7 mm, and in more specific embodiments, from about 4.5 to about 6 mm, or even more specifically from about 5.1 to about 5.6 mm. As with the previous aspect, any of the above-described variants in the catalyst support may be used. Thus, for example, the support may have a surface area of about 200 to about 250 $m^2/g$, or surface area of about 225 $m^2/g$. In one or more embodiments, the support may comprise about 2 wt-% alumina.

Again, Pd and Au may be deposited with an aqueous solution containing compounds of both elements. Thus, in one embodiment, depositing Pd and Au onto the support to form a catalyst layer on the support comprises impregnating the support with a solution containing chloride salts of Pd and Au and subsequently contacting the support with a basic solution. Alternatively, separate solutions may be used, one containing a Pd compound and the other a gold compound. Examples of suitable water-soluble Pd compounds include, but are not limited to, palladium (II) chloride, sodium palladium (II) chloride and palladium (II) nitrate. Examples of suitable water-soluble Au compounds include, but are not limited to, gold (III) chloride and tetrachloroauric (III) acid.

The resulting amounts of catalyst can be calculated to achieve the desired amount of Au and/or Pd. Thus, for example, in one or more embodiments, the Pd is present in an amount of about 3 to about 10 grams per liter of catalyst composition and/or the Au is present in an amount of about 0.9 to about 5 grams per liter of catalyst composition. In one or more embodiments, the ratio of Au to Pd is about 0.3 to about 0.5.

The process may further comprise washing the support with eggshell layer to remove residual alkali metals and halogens leftover from the precursor and then drying the support with eggshell catalyst layer.

In one or more embodiments, the catalyst layer on the support is reduced at a temperature of about 200 to about 500° C. in a reducing gas comprising about 4% to about 100% hydrogen gas for about 1 to about 4 hours. In a further embodiment, the catalyst layer is reduced for about 2 to about 3 hours. In some embodiments, the reducing gas may further comprise nitrogen gas or ethylene. In further embodiments, the nitrogen and hydrogen gases are present in a ratio from about 5 to 1. In one or more embodiments, the reducing gas contains pure hydrogen. In one embodiment, the term "reducing gas" in this context is in the flammable regime.

In one or more embodiments, the support with eggshell catalyst layer is impregnated with potassium acetate after reduction. This may be carried out after depositing Pd and/or Au by covering the eggshell catalyst layer with a solution of the potassium acetate. In one embodiment, impregnating the catalyst layer on the support with potassium acetate comprises impregnating the support with a solution containing potassium acetate and drying said support. In one or more embodiments, drying the support comprises drying under vacuum.

Application

The catalyst composites described herein may be used for the production of vinyl acetate monomer. Accordingly, another aspect of the invention relates to a method of producing vinyl acetate monomer. The method comprises contacting a gas comprising ethylene, acetic acid and oxygen with a catalyst composition comprising a support comprising silica and about 1 to about 3 wt-% alumina, wherein the support has a surface area of about 175 to about 300 $m^2/g$; and a catalyst comprising Au or Pd.

The catalyst composition may be contacted with the gas as part of a fixed bed type reactor. Typically, the catalyst composites, which are commonly in the form of small spheres, are poured into a fixed bed reactor. Then, the reagent gas is allowed to flow through, thereby allowing contact between the gas and catalyst composites.

Any of the variations in catalyst composites described above may be used to produce the vinyl acetate monomer. In one or more embodiments, improvements of 15-30% in space-time-yield have been achieved over currently available catalyst composites.

In one or more embodiments, the catalyst compositions described herein may be used in other reactions. Such reactions include, but are not limited to, those involving olefins, oxygen, and carboxylic acid.

EXAMPLES

Without intending to limit the invention in any manner, embodiments of the present invention will be more fully described by the following examples.

Example C1

A comparative example was prepared using a commercial support. The support had an alumina content of 3 wt-%, and a surface area of 150 $m^2/g$. The 5.0-5.3 mm spheres were first spray impregnated with sodium palladium chloride and sodium gold chloride salt solutions and deionized (DI) water to incipient wetness. The Pd and Au were precipitated by soaking the wet impregnated spheres in a basic solution of sodium metasilicate and DI water. In order to ensure the proper eggshell thickness and complete precipitation 8 moles of sodium metasilicate was added for every mole of metal to be precipitated. This led to a 500 micrometers eggshell.

After precipitation, the spheres were washed to remove residual sodium and chloride to levels below 100 microsiemens per centimeter in the wash water. After which, the support with an eggshell layer was dried at 150° C. for 12 hrs.

The catalytic metals were then reduced at 118° C. with 80% $H_2$ in $N_2$.

Finally, the catalyst is impregnated to incipient wetness with an aqueous solution of potassium acetate and vacuum dried at 100° C. until the resulting catalyst contained less than 2% water.

Example 1

Similar to the procedure outlined for Example C1, a catalyst composite was prepared using a support having an alumina content of 1 wt % and a surface area of 225 m²/g. The support was spray impregnated with Pd and Au and then soaked in an aqueous solution of sodium metasilicate to form an eggshell layer, followed by washing and drying. The catalyst was then reduced at 100° C. for 2 hrs in 80% $H_2$ in $N_2$, followed by an impregnation with potassium acetate and vacuum drying.

Example 2

Similar to the procedure outlined for Example C1, a catalyst composite was prepared using a support having an alumina content of 2 wt % and a surface area of 225 m²/g. The support was spray impregnated with Pd and Au and then soaked in an aqueous solution of sodium metasilicate to form an eggshell layer, followed by washing and drying. The catalyst was then reduced at 100° C. for 2 hrs in 80% $H_2$ in $N_2$, followed by an impregnation with potassium acetate and vacuum drying.

Example 3

Similar to the procedure outlined for Example C1, a catalyst composite was prepared using a support having an alumina content of 3 wt % and a surface area of 225 m²/g. The support was spray impregnated with Pd and Au and then soaked in an aqueous solution of sodium metasilicate to form an eggshell layer, followed by washing and drying. The catalyst was then reduced at 100° C. for 2 hrs in 80% $H_2$ in $N_2$, followed by an impregnation with potassium acetate and vacuum drying.

Results of Examples 1-3 and C1

Examples 1-3 and C1 were tested in an isothermal stacked pellet "differential" reactor. The reported results are after 20 hours of operation. The operating conditions for the reactor were as follows:
Temperature=150° C.
Pressure=120 PSIG
GHSV=35,000 hr$^{-1}$
Catalyst Bed Size=7.76 mL (50-80 pellets)
Feed Composition:
  72% Ethylene
  20% Acetic Acid
  7% Oxygen
  1% Water Results from the performance testing are tabulated as turnover number (TON) (also referred to as turnover frequency) [mol VAM/mol Pd/hr] and ethylene selectivity. The TON was calculated to correct for differences in metal loading. The Pd was assumed to be fully dispersed. It was not possible to measure the Pd dispersion because of the confounding effects from the Au and potassium acetate present on the catalyst. The results are shown below in Table 1:

| Example | $Al_2O_3$ (wt-%) | TON (mol VAM/mol Pd/hr) | Selectivity (%) |
|---|---|---|---|
| C1 | 3 | 327 | 94.3 |
| 1 | 1 | 381 | 93.2 |
| 2 | 2 | 434 | 93.8 |
| 3 | 3 | 373 | 93.8 |

As shown in Table 1, Examples 1-3 provide much more active catalysts than the comparative example. Examples 1 and 3 provided around a 50 mol VAM/mol Pd/hr higher space-time-yield, while Example 2 provided an increase of almost 107 mol VAM/mol Pd/hr.

Example C2

A second comparative example was prepared using a commercial support. The support had an alumina content of 3 wt-%, and a surface area of 150 m²/g. The support was used to produce a catalyst composite by using an optimized preparation technique. The eggshell layer was prepared, washed, and dried as with C1, but the catalyst was reduced at 230, 300, 350, 400, and 500° C. in 20% $H_2$ for 2 to 3 hours. The catalyst precursor was then impregnated with potassium acetate and vacuum dried to reduce the water content to below 2%.

Example 4

An example was prepared with a support having an alumina content of 2 wt-%, and a surface area of 225 m²/g. The support was used to produce a catalyst composite by using an optimized preparation technique. Pd and Au were deposition precipitated as with Examples 1-3, but the catalyst was reduced at 200, 300, 400, and 500° C. in 20% $H_2$ for 2 to 3 hours. The catalyst precursor was then impregnated with potassium acetate and vacuum dried to reduce the water content to below 2%.

Results of Examples C2 and 4

Examples C2 and 4 were tested as described above for examples 1-3 and C1. The FIGURE shows the TON versus the reduction temperature, and the percentages of the FIGURE show the ethylene selectivity. As seen in the FIGURE, the TON of Example 4 is consistently and significantly higher compared to the comparative example. Additionally, the data demonstrates that as the reduction temperature is increased, the TON also increases for both supports. Even with the increase in the space-time-yield, Example 4 maintains a higher yield than C2. Example 4 also demonstrates comparable selectivity.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of making a catalyst composite, the method comprising:
   providing a spherical support material comprising silica and about 1 to about 3 wt-% alumina, wherein the spherical support material has a surface area of about 175 to about 300 $m^2/g$, and a diameter of about 3 mm to about 7 mm;
   depositing Pd and Au onto the support material to form a catalyst composite precursor comprising:
   an inner region; and
   an outer region;
   wherein:
      the outer region having a depth from the surface to about 500 µm of the spherical support material;
      the outer region comprising the Pd and Au; and
      the inner region being free of the Pd and Au;
   reducing the catalyst composite precursor at a temperature of about 400° C. to about 500° C. in a reducing gas comprising about 20% to about 100% hydrogen gas for about 1 to about 4 hours to form a reduced catalyst composite precursor;
   and impregnating the reduced catalyst composite precursor with potassium acetate to form the catalyst composite.

2. The method of claim 1, wherein the reducing gas further comprises nitrogen gas or ethylene.

3. The method of claim 2, wherein the nitrogen and hydrogen gases are present in a ratio from about 5 to 1 to less than pure hydrogen.

4. The method of claim 1, wherein the spherical support material has a surface area of about 200 to about 250 $m^2/g$.

5. The method of claim 1, wherein the depositing comprises impregnating the support material with a solution containing chloride salts of Pd and Au and subsequently contacting the support material with a basic solution.

6. The method of claim 1, wherein the impregnating comprises impregnating the spherical support material with a solution containing potassium acetate and drying the catalyst composite under vacuum.

7. The method of claim 1, wherein the spherical support material comprising silica and about 2 wt % alumina.

* * * * *